United States Patent
Torp et al.

(10) Patent No.: US 6,618,493 B1
(45) Date of Patent: Sep. 9, 2003

(54) METHOD AND APPARATUS FOR VISUALIZATION OF MOTION IN ULTRASOUND FLOW IMAGING USING PACKET DATA ACQUISITION

(75) Inventors: Hans Garmann Torp, Trondheim (NO); Steinar Bjaerum, Trondheim (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/449,391

(22) Filed: Nov. 26, 1999

(51) Int. Cl.$^7$ .................................................. G06K 9/00
(52) U.S. Cl. ...................... 382/131; 382/107; 382/263; 600/443; 600/454
(58) Field of Search ................................ 382/128, 131; 128/915, 916; 600/443, 437, 447, 449, 453, 454, 455

(56) References Cited

U.S. PATENT DOCUMENTS

| | | | |
|---|---|---|---|
| 4,888,694 A | 12/1989 | Chesarek | 364/413.24 |
| 5,669,387 A | 9/1997 | Mine | 600/447 |
| 5,701,897 A | 12/1997 | Sano | 600/443 |
| 5,961,461 A | * 10/1999 | Mo et al. | 600/443 |
| 6,012,458 A | * 1/2000 | Mo et al. | 600/437 |
| 6,132,376 A | 10/2000 | Hossack et al. | 600/443 |
| 6,267,725 B1 | * 7/2001 | Dubberstein | 600/443 |
| 6,277,075 B1 | * 8/2001 | Torp et al. | 600/443 |
| 6,383,139 B1 | * 5/2002 | Hwang et al. | 600/441 |

OTHER PUBLICATIONS

Ferrara et al., "Color flow mapping," Ultrasound Med. Biol., vol. 23, No. 3, pp. 321–345, 1997.

Kasai et al., "Real–time two–dimensional blood flow imaging using an autocorrelation technique," IEEE Trans. Sonics Ultrason., vol. 32, No. 3, pp. 458–464, May 1985.

Fox, "Multiple crossed–beam ultrasound Doppler velocimetry," IEEE Trans. Sonics Ultrason., vol 25, No. 5 pp. 281–286, Sep. 1978.

Newhouse et al., "Ultrasound Doppler probing of flows transverse with respect to beam axis," IEEE Trans. Biomed. Eng., vol. 34, No. 10, pp. 779–789, Oct. 1987.

Trahey et al., "Angle independent ultrasonic detection of blood flow," IEEE Trans. Biomed. Eng., vol. 34, No. 12, pp. 965–967, Dec. 1987.

Jensen et al., "A new method for estimation of velocity vectors," IEE Trans. Ultrason., Ferroelect., Freq. Contr., vol. 45, No. 3, pp. 837–851, May 1998.

Anderson, "Multi–dimensional velocity estimation with ultrasound using spatial quadrature," IEEE Trans. Ultrason., Ferroelect., Freq. Contr., vol. 45, No. 3, pp. 852–861, 1998.

* cited by examiner

*Primary Examiner*—Jon Chang
*Assistant Examiner*—Charles Kim
(74) *Attorney, Agent, or Firm*—Ostrager Chong & Flaherty LLP

(57) ABSTRACT

A method and an apparatus for imaging blood motion by displaying an enhanced image of the fluctuating speckle pattern. The first step in the blood motion image processing is high-pass filtering of the signal vector from each range gate. Following high-pass filtering, a speckle signal is formed. The speckle signal is then subjected to a nonlinear scale conversion. The resulting speckle signal is displayed as the desired blood motion image concurrently with a corresponding tissue image.

35 Claims, 13 Drawing Sheets

METHOD AND APPARATUS FOR VISUALIZATION OF MOTION IN ULTRASOUND FLOW IMAGING USING PACKET DATA ACQUISITION

FIELD OF THE INVENTION

This invention generally relates to ultrasound imaging of the human anatomy for the purpose of medical diagnosis. In particular, the invention relates to methods and apparatus for imaging blood vessel structures, and more particularly, to signal processing algorithms for visualization of blood movement for use in ultrasound imaging systems.

BACKGROUND OF THE INVENTION

Conventional color flow imaging, including "angio" or "power Doppler imaging" (referred to hereinafter as "flow imaging"), produces one image from a sequence of transmitted pulses (a packet), typically in the range of 5–15 pulses for each scan line in the image. Slowly moving muscular tissue produces lower Doppler shift in the received signal than signal from moving blood, and efficient clutter filters are designed to suppress the clutter signal to a level much lower than the signal from blood. The signal power after clutter filtering is used to detect points in the image where blood is present. An alternative is to display the signal power as an image (angio or power Doppler) to visualize blood vessels. In order to get reliable detection, substantial temporal and spatial averaging is used, thus limiting the dynamic variation, as well as spatial resolution (bleeding). This averaging process suppresses the spatial speckle pattern in the signal amplitude.

Conventional ultrasound blood flow imaging is based on detection and measurement of the Doppler shift created by moving, scatterers. This Doppler shift is utilized to suppress the signal from slowly moving muscular tissue, in order to detect the presence of blood, and is also used to quantify the actual blood velocity in each point of an ultrasound image. Unfortunately, the Doppler frequency shift is only sensitive to the velocity component along the ultrasonic beam; possible velocity components transverse to the beam are not detected or measurable from the received signal Doppler spectrum. In standard color flow imaging, the Doppler shift is estimated from the received signal generated by a number of transmitted pulses, and coded in a color scale. In some situations, the blood flow direction can be measured from the vessel geometry, but this is difficult to do in an automatic way, especially when the vessel geometry is not clearly visible in the image. Standard color flow imaging often gives confusing blood velocity visualization; e.g., in a curved blood vessel the Doppler shift, and therefore also the color, is changing along the vessel due to change in the angle between the blood velocities and the ultrasonic beam, even though the velocity magnitude is constant. In power Doppler (also called the angio mode) this problem is solved by discarding the measured Doppler shift from the display.

There is considerable interest in measuring the transverse velocity component in ultrasound flow imaging, and a number of methods have been proposed. Compound scanning from two different positions was disclosed by Fox in "Multiple crossed-beam ultrasound Doppler velocimetry," IEEE Trans. Sonics Ultrason., Vol. 25, pp. 281–286, 1978. Compound scanning from two different positions gives two velocity components, but there are practical problems with the large-aperture transducer, the time lag between the measurement of the two components, and the limited field of view. In accordance with a method disclosed by Newhouse et al. in "Ultrasound Doppler probing of flows transverse with respect to beam axis," IEEE Trans. Biomed. Eng., Vol. 34, pp. 779–789, October 1987, the transit time through the ultrasound beam is measured, which is reflected in an increased bandwidth of the Doppler signal. This method has very low accuracy, does not yield flow direction, and will only work in regions with rectilinear and laminar flow. Two-dimensional speckle tracking methods based on frame-to-frame correlation analysis have been proposed by Trahey et al. in "Angle independent ultrasonic detection of blood flow," IEEE Trans. Biomed. Eng., Vol. 34, pp. 965–967, December 1987. This method can be used both for the RF signal and the amplitude-detected signal. Coherent processing of two subapertures of the transducer to create lateral oscillations in the received beam pattern has been described by Jensen et al. in "A new method for estimation of velocity vectors," IEEE Trans. Ultrason., Ferroelect., Freq. Contr., Vol. 45, pp. 837–851, May 1998, and by Anderson in "Multi-dimensional velocity estimation with ultrasound using spatial quadrature," IEEE Trans. Ultrason., Ferroelect., Freq. Contr., Vol. 45, pp. 852–861, May 1998. This method gives quantitative lateral velocity information, including the sign. The main drawback of this method is poor lateral resolution, which limits its use for imaging.

There is a need for a method of ultrasound imaging which gives the system user a correct perception of the blood flow direction and magnitude, and which is also useful to separate true blood flow from wall motion artifacts.

SUMMARY OF THE INVENTION

In ultrasound imaging, the returned echoes are processed coherently. In the images there are variations in the intensity due to constructive and destructive interference of the sound waves scattered back from a large number of scatterers. These variations in the intensity is often termed the "speckle pattern". When there is a slight displacement of the scatterers (red blood cells), there will be a corresponding displacement of the speckle pattern. By enhancing the speckle pattern from moving scatterers and display a stream of such images, an intuitive display of the blood flow is obtained.

The present invention comprises a method and an apparatus for imaging blood motion by preserving, enhancing and visualizing speckle pattern movement, which is related to the blood cell movement in the blood vessels. This method will be referred to herein as "blood motion imaging" (BMI). Speckle pattern movement gives the user a correct perception of the blood flow direction and magnitude, and is also useful to separate true blood flow from wall motion artifacts. In this way, the system operator can see the blood flowing in the image, although no attempt is made to measure the lateral velocity component. However, the lateral velocity component may be derived indirectly by combining an angle measurement derived from the speckle motion with the radial velocity component obtained from the Doppler frequency shift.

In one preferred embodiment of the invention, multiple image frames per packet of transmitted pulses are produced, instead of a single image frame. The motion of the blood scatterers creates a corresponding movement of the speckle pattern in the images from frame to frame, showing both radial and lateral movement. The time between each of these frames equals the pulse repetition time (1/PRF) within the signal packets. In order to visualize the motion, the display frame rate must be reduced substantially, e.g., from 1 kHz to 30 Hz. For real-time display, much data must be discarded, but for slow motion replay, a larger fraction or all of the recorded frames can be used.

In accordance with the preferred embodiment of the invention, the data are acquired as in conventional color flow imaging. A series of pulses (a packet) are transmitted in each beam direction and echoes are acquired for a region of interest (ROI) in the blood motion image. The pulse firings within a packet are separated by a constant time interval. This time interval is much smaller than the time between successive packets. Then one tissue image, which may extend beyond the blood motion image ROI, is recorded. The maximum possible pulse repetition frequency (PRF) during packet acquisition is determined by the imaging depth. By reducing the PRF, it is possible to use a technique called beam interleaving. After firing a pulse in a first direction, there is time available to fire pulses in one or more different directions before firing the next pulse in the first direction. This collection of beam directions is called an interleave group. By using a relatively broad transmit beam, it is possible to acquire several receive beams per transmit beam by simultaneous beamforming in slightly different directions. This known technique is called multi-line acquisition (MLA).

The data input for signal processing are the beamformed and complex-demodulated I/Q data samples. Alternatively, the processing can be performed on the real-valued RF data without complex demodulation. In accordance with the processing technique disclosed herein, several images per packet are displayed, as opposed to conventional color flow imaging in which only one image per packet is displayed. The first step in the BMI processing is high-pass filtering of the signal vector from each range gate. Following high-pass filtering, the speckle signal is formed. The speckle signal is then subjected to a nonlinear scale conversion. An example of this is logarithmic compression followed by gain and dynamic range adjustment. The resulting speckle signal is displayed as the desired blood motion image concurrently with a corresponding tissue image.

In accordance with another preferred embodiment, fluctuation in the mean power from packet to packet is compensated for in order to obtain a smooth temporal display. This is accomplished by dividing each speckle signal sample by the mean value calculated for the packet, thereby forming an enhanced speckle signal for imaging blood motion. In the log domain this is equivalent to subtracting the logarithm of the mean value from the logarithm of each speckle signal sample.

In general, time averaging will reduce the speckle variation. However, time averaging within one packet will produce a trace pattern in the image along the blood flow direction which show the direction of flow even in a still frame image. Further time averaging (between packets), which is usually done in conventional color flow imaging, will destroy this trace pattern.

Therefore, in accordance with a further preferred embodiment, the moving speckle patterns are processed temporally. As a result of the temporal processing, the moving speckle patterns create traces in the image along the streamlines in the flow. Simple temporal averaging within each packet gives a non-directive streamline effect. More sophisticated methods can also preserve direction information, and to some extent velocity magnitude. Temporal processing is not necessary for the visual perception of flow, but makes possible still frame visualization of flow direction and magnitude, and may give improvement for real-time display, where the frame rate must be limited. If the smoothing window for temporal averaging is chosen equal to the packet size, and one image is generated for each packet, the processing would be similar to standard color flow imaging. However, a number of steps may preferably be taken to accentuate the speckle pattern in the flow image. First, the spatial resolution should be as high as possible by using a short transmitted pulse and a large-aperture transducer. Second, the number of scan lines per beam interleave group should be as high as possible. This can be achieved by using a low PRF and/or MLA (parallel receive beams). Third, the speckle signal can be normalized by a local average obtained by temporal and/or spatial averaging.

There are various ways of including the speckle pattern in the flow image: (1) by combining the speckle signal with the signal power and showing the combined signal in the same way as the angio mode flow image; (2) by intensity ("value" in HSV color representation) modulation of the color flow or angio image; (3) by color coding the "age" of the speckle, in order to visualize the direction and the magnitude of the movement.

The invention can be implemented as post-processing, based on recorded I/Q data of a sequence of images, or in real-time. The invention can be implemented in hardware or software.

DETAILED DESCRIPTION OF THE PREFERRED EMBODIMENTS

Figure 1:
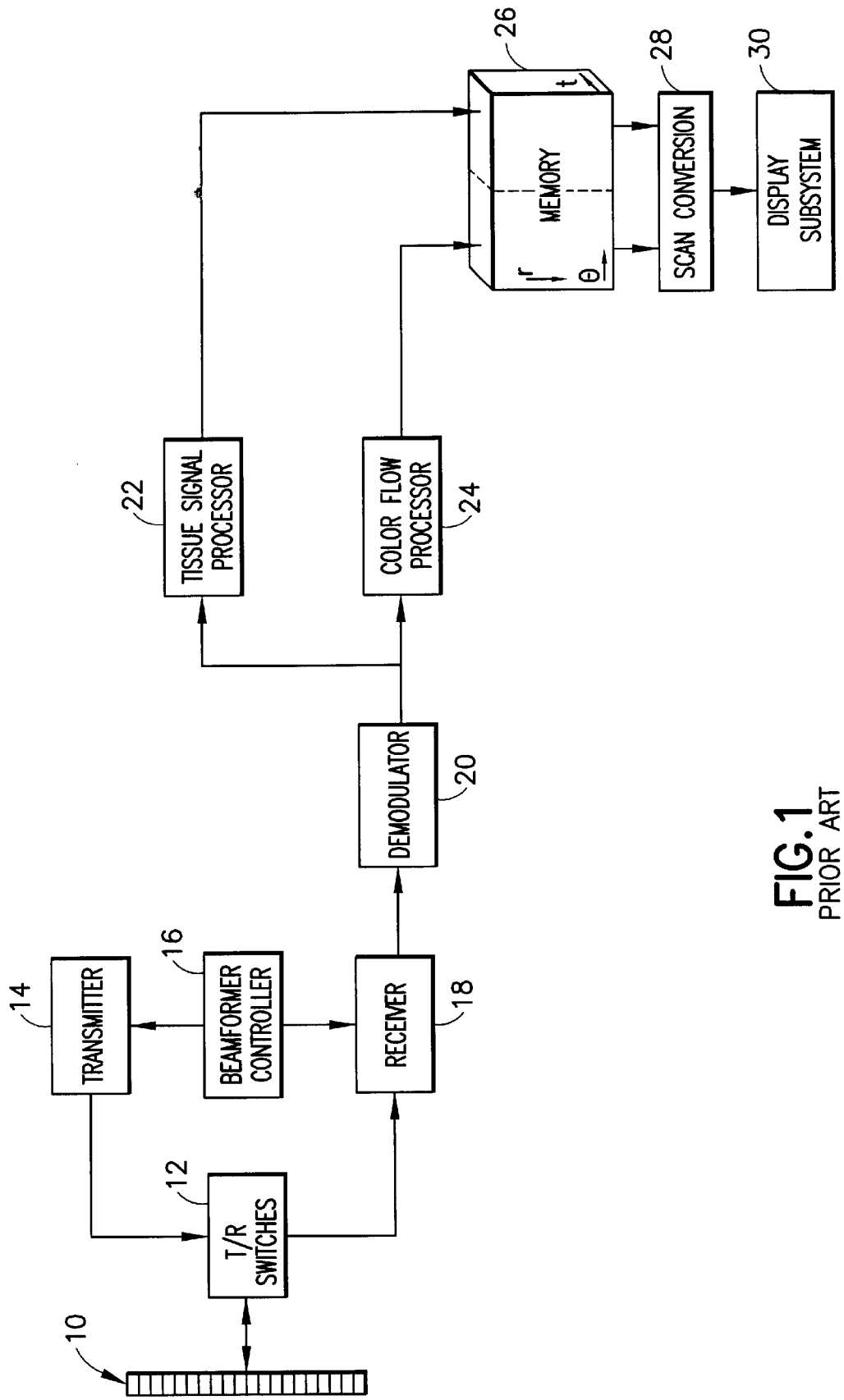
FIG. 1 is a block diagram showing a conventional ultrasound imaging system capable of superimposing a color flow image on a tissue image.

A typical ultrasound imaging system having color flow and tissue imaging is generally depicted in FIG. 1. The individual elements of an ultrasound transducer array 10 are activated by a multiplicity of pulsers of a transmitter 14 via transmit/receive (T/R) switches 12 to transmit wavelets which are focused at the same transmit focal position with the same transmit characteristics to form a transmit beam. The transmit sequences and time delays for activating the pulsers to achieve transmit beamforming are provided by a beamformer controller 16 (e.g., incorporated as software in a host computer). Each transmit beam propagates through the object being scanned and is reflected by ultrasound scatterers in the object back to the array. After each transmit firing, the echo signals detected by the transducer array elements are fed to respective receive channels of the receiver 18. The receiver 18 beamforms the echoes under the direction of the beamformer controller 16. The receiver 18 imparts the proper receive focus time delays to the received echo signal and sums them to provide an echo signal which accurately indicates the total ultrasonic energy reflected from a succession of ranges corresponding to a particular transmit focal zone.

In an RF system, the beamsummed RF echo signals output by the receiver 18 are sent to a tissue signal (e.g., B-mode) processor 22. The tissue signal processor typically incorporates an envelope detector for forming the envelope of the beamsummed signal. The envelope of the signal undergoes some additional tissue signal processing, such as logarithmic compression, to form display data which is stored in a memory 26 and then output to a scan converter 28. Alternatively, as shown in FIG. 1, the RF signal is demodulated to baseband by a demodulator 20, and then the in-phase and quadrature components are processed separately by the tissue signal processor.

In general, the display data is converted by the scan converter 28 into X-Y format for video display. Each frame of intensity data, representing one of a multiplicity of parallel scans or slices through the object being examined, is stored in the scan converter 28 and in the next cycle is transmitted to video processor in the display subsystem 30. The video processor maps the video data to a gray scale for video display. The gray-scale image frames are then sent to the video monitor of the display subsystem 30.

In the color flow imaging mode, a color flow processor 24 processes data acquired during additional scans, each color flow image being acquired from multiple scans. For example, a sequence of N pulses (i.e., a "packet") are transmitted to each focal position in the ROI, one color flow image being generated for each packet of scans. The color flow image data is stored in a separate part of memory 26, scan converted, video processed using a color mapping and then superimposed on the tissue image during display.

Figure 2:
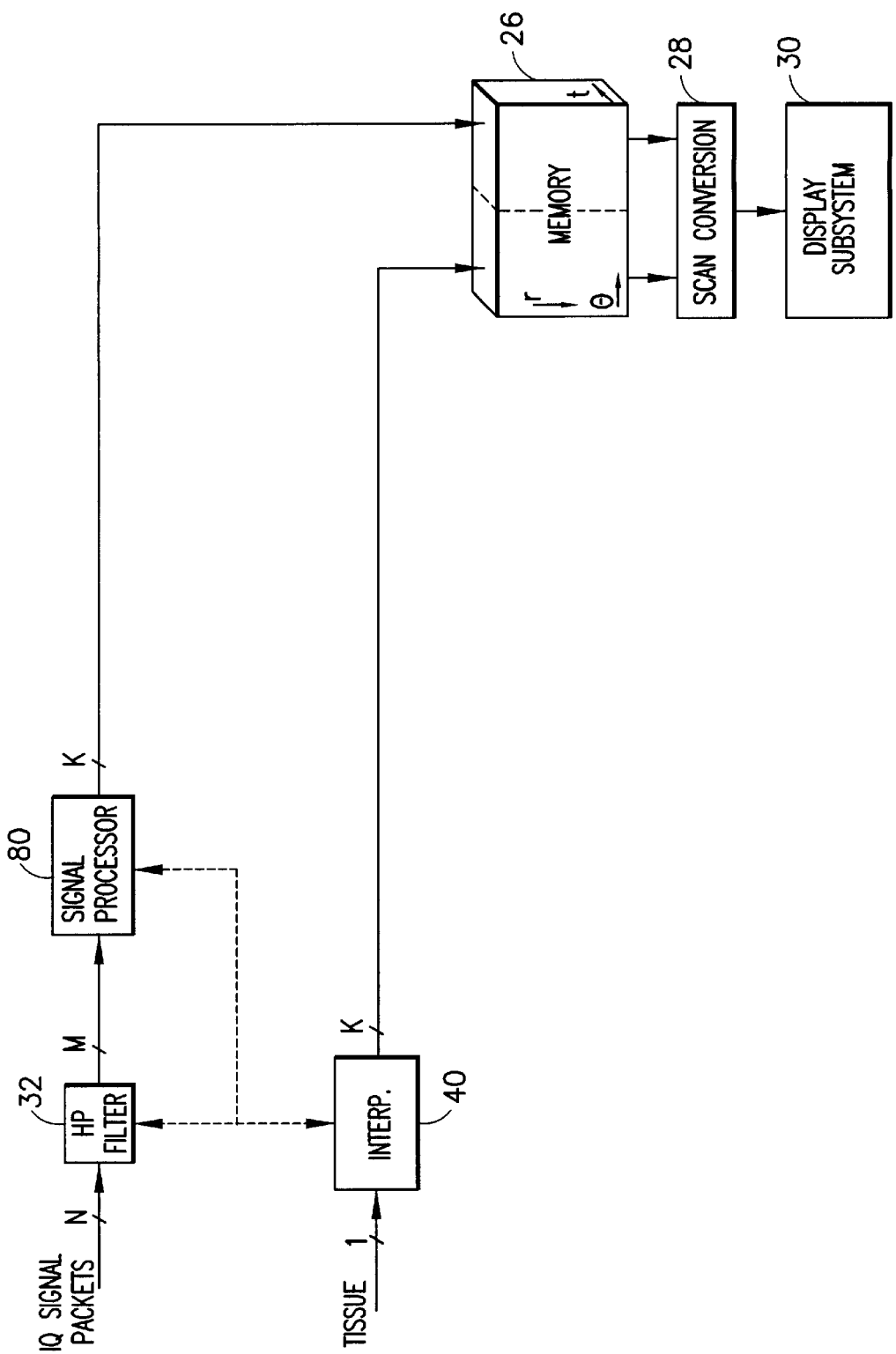
FIG. 2 is a block diagram showing the most general form of the invention for imaging based on separate blood motion and tissue scans.

The most general form of the invention is depicted in FIG. 2, with the understanding that the inputs labeled "Tissue" and "IQ Signal Packets" are both received from the demodulator depicted in FIG. 1. In accordance with this and other preferred embodiments, the data are acquired as in conventional color flow imaging (e.g., using the blocks upstream of demodulator 20 in FIG. 1). A series of N pulses (one packet with packet size N) are transmitted in each beam direction of the flow image. Then one tissue image is recorded. The maximum possible pulse repetition frequency (PRF) is determined by the imaging depth.

In accordance with the processing technique depicted in FIG. 2, several images per packet are displayed, as opposed to conventional color flow imaging in which only one image per packet is displayed. The BMI processing shown in FIG. 2 (and later figures) is for one depth range, but the same processing is applied to all depth ranges in parallel. The data samples acquired from each range gate (following a packet of transmits) are filtered by a digital high-pass filter 32. The digital high-pass filter is applied individually to each signal sample in the set of N beam vectors. More precisely, if each beam vector consists of L signal samples, representing L depth ranges, the set of received signal samples can be described as a matrix $s(l,n)$, $l=1, \ldots, L$, $n=1, \ldots, N$. Now for each depth range l, the signal samples $s(l,1), \ldots, s(l,N)$ are input to the high-pass filter 32. The high-pass filter 32 is working independently for each depth range l. The output of the high-pass filter for all depth ranges will then be M beam vectors, where $M \leq N$. The filter used here works in the same way as the clutter filter used in conventional color flow imaging.

The simplest type of filter that can be used is a Finite Impulse Response (FIR) filter. Such a filter is described by an impulse response function $h(n)$, $n=, \ldots, J-1$, where J is the filter length. The relation between J, N, and M in FIG. 2 is given by $M=N-J+1$. If the input signal is $x(n)$ and the output signal is $y(n)$, then the filtering operation is given by $$y(n) = \sum_{k=0}^{J-1} h(k)x(n-k)$$

Each output sample $y(n)$ is a weighted sum of the previous J input samples $x(n)$. The output sample $y(0)$ is given by $$y(0)=h(0)x(0)+h(1)x(-1)+ \ldots +h(J-1)x(-J+1)$$

and depends on $x(n)$ for $n<0$. The output sample $y(J-1)$ is $$y(J-1)=h(0)x(J-1)+h(1)x(J-2)+ \ldots +h(J-1)x(0)$$

and is the first output sample that does not depend on any $x(n)$ for $n<0$. In the present case the input signal is not available for $n<0$. This means that the first valid output sample is $y(J-1)$. In the example shown in FIG. 12, the number of input samples is $N=6$. With an FIR filter of length $J=4$, the number of valid output samples is $M=N-(J-1)=3$. An example of a high-pass impulse response function of length $J=4$ is given by $$h(0)=0.16, \ h(1)=0.53, \ h(2)=-0.53, \ h(3)=-0.16$$

The filtering operation can be generalized to include all linear filters by using a matrix notation. Let the input signal be written as an N-dimensional vector x:

$$x = \begin{bmatrix} x(0) \\ x(1) \\ \vdots \\ x(N-1) \end{bmatrix}$$

A general linear filtering operation is then described by a matrix multiplication of the vector x. Let the filter matrix A be of dimension M×N. This filter will produce an M-dimensional output vector y given by $y=Ax$. In the FIR-filter example discussed above, the filter matrix A is given by $$A = \begin{bmatrix} h(3) & h(2) & h(1) & h(0) & 0 & 0 \\ 0 & h(3) & h(2) & h(1) & h(0) & 0 \\ 0 & 0 & h(3) & h(2) & h(1) & h(0) \end{bmatrix}$$

It is emphasized that a general filter matrix is not limited to the FIR structure shown above. IIR filters with different initialization techniques, and polynomial regression filters are other examples of filters that may be used. If an FIR filter is used, the first J−1 samples, where J is the FIR filter length, must be discarded. If an IIR filter is used, several initialization techniques exist to suppress the filter transient, but some of the first samples may have to be discarded.

In FIG. 2, the input to the high-pass filter 32 consists of N samples, where N is equal to the packet size, while the output consists of M samples, where 1<M≦N. Following high-pass filtering, there is further signal processing (block 80) which may reduce the number of samples to K where 1<K≦M.

Figure 3:
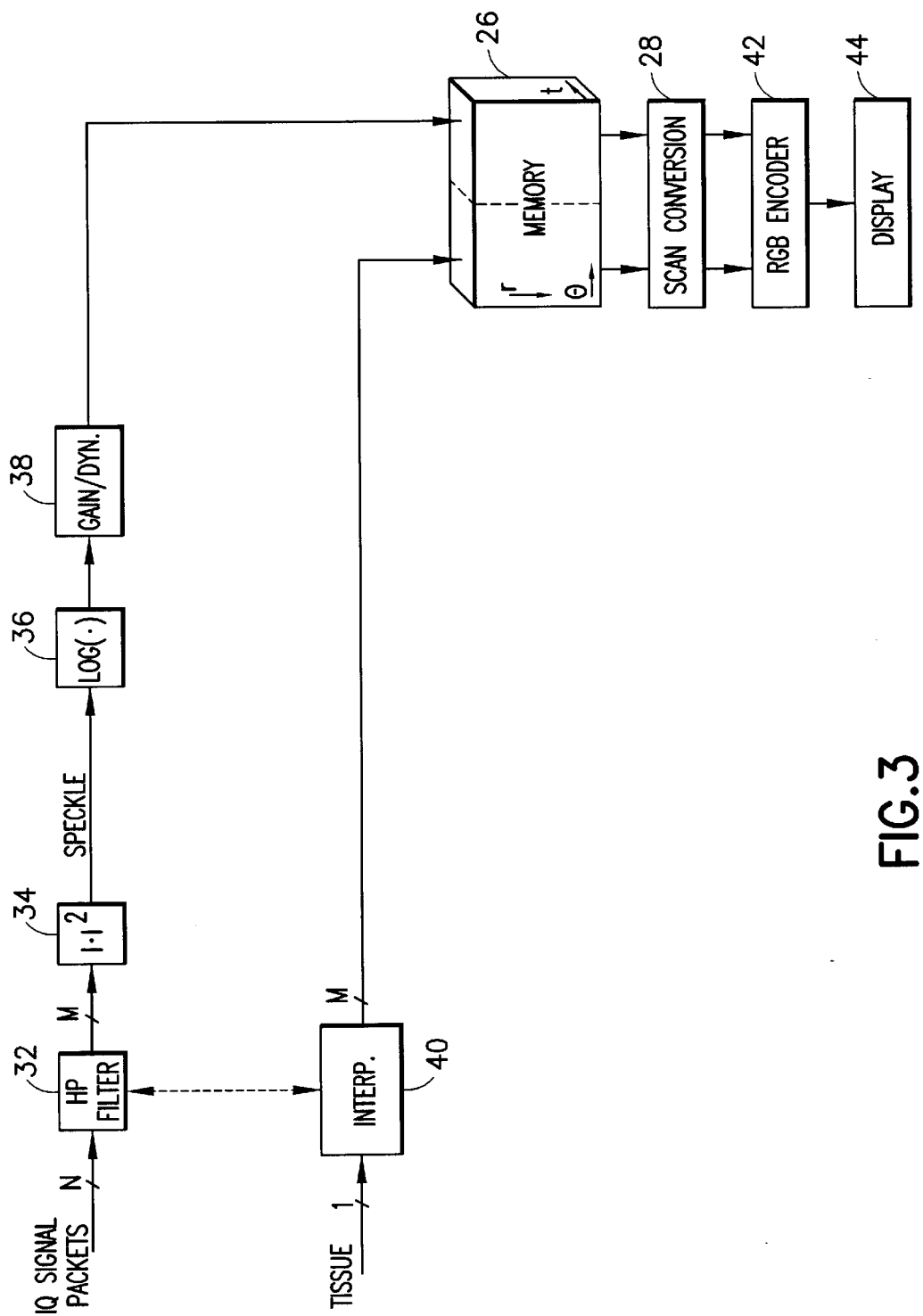
FIG. 3 is a block diagram showing one preferred embodiment of the invention for imaging based on separate blood motion and tissue scans.

In FIG. 3, one preferred embodiment of the signal processor in FIG. 2 is shown. The signal is amplitude detected, thereby forming what will hereinafter be referred to as the "speckle signal". In the example in FIG. 3, the squared magnitude (i.e., power) of each of the M output samples is calculated in signal magnitude processor 34. If the complex I/Q signal is given by x(k)=z(k)+iy(k), where z and y are real and i=√−1, then the output of processor 34 is given by $z(k)^2+y(k)^2$. In the notation shown inside processor 34, the center dot is replaced by the input signal x(k). The speckle signal is then subjected to a nonlinear amplitude transformation. In FIG. 3 this transformation consists of logarithmic compression (block 36) followed by gain and dynamic range adjustment (block 38). The resulting speckle signal is stored in memory 26.

In accordance with the preferred embodiment shown in FIG. 3, a separate scan is performed to acquire the tissue (e.g., B-mode) image in a conventional manner. One tissue scan is performed for each packet of N BMI scans. The acquired tissue scan data is interpolated by an interpolator 40 to generate M tissue images for every M blood motion images. The M tissue images are stored in a separate part of memory 26. Each tissue image and each blood motion image are scan converted by scan converter 28 and sent to the RGB encoder 42. A simple combination of the blood motion image and the tissue image can be used for the RGB components of the image displayed by the display subsystem 44. One example is: R=4×BMI+2×tissue; G=BMI+4×tissue; and B=4×tissue. A combination producing a grayscale image is also possible.

Figure 4:
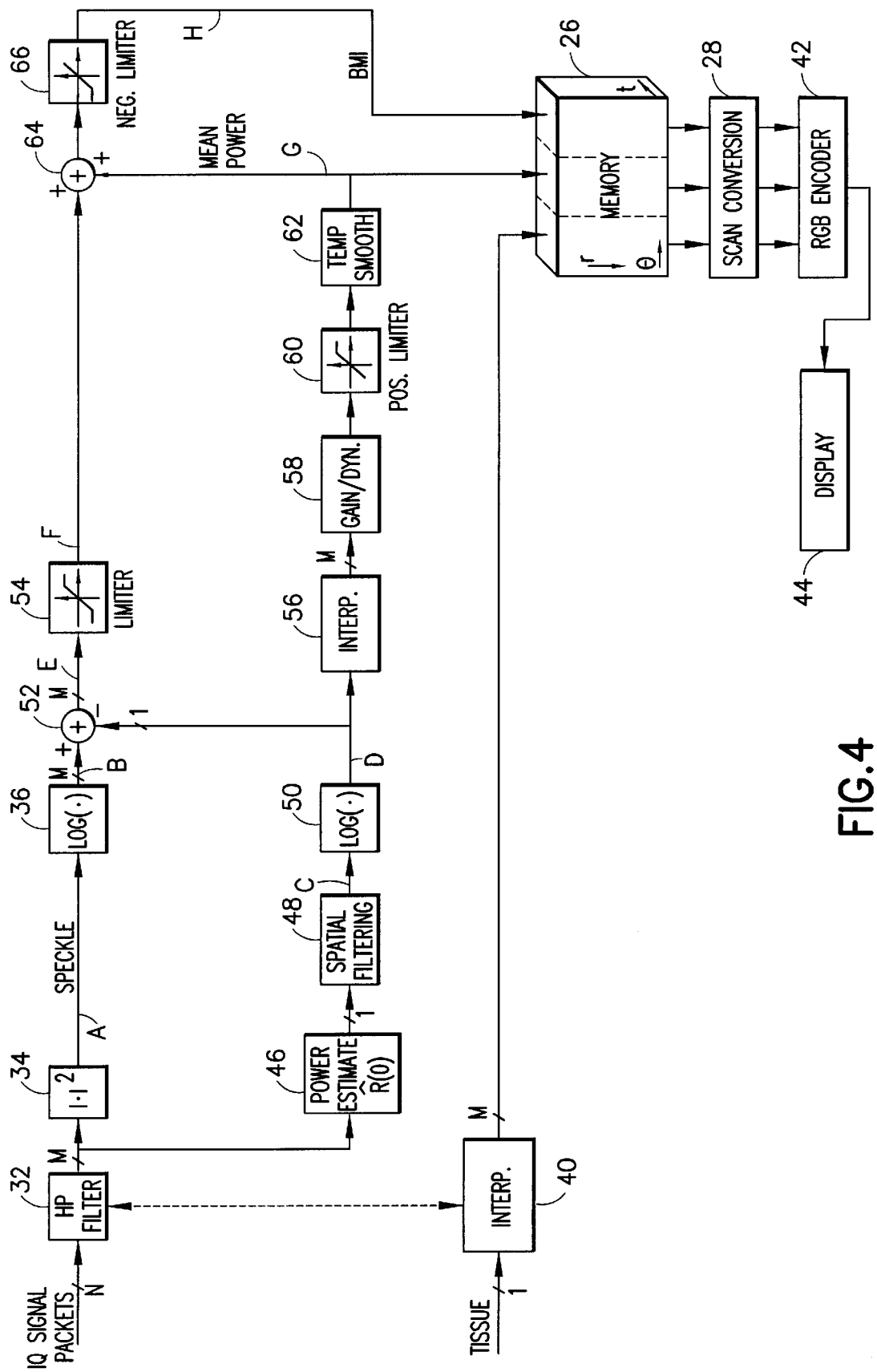
FIG. 4 is a block diagram showing another preferred embodiment of the invention which utilizes amplitude normalization to obtain a smoother display.

FIG. 4 shows a further preferred embodiment in which the speckle signal is enhanced by amplitude normalization to provide a smoother display. In particular, fluctuation in the mean power from packet to packet is compensated for in order to obtain a smooth temporal display. This is accomplished by dividing each speckle signal sample by the mean value calculated for the packet, thereby forming an enhanced speckle signal for imaging blood motion. In the log domain this is equivalent to subtracting the logarithm of the mean value from the logarithm of each speckle signal sample.

Figure 6:
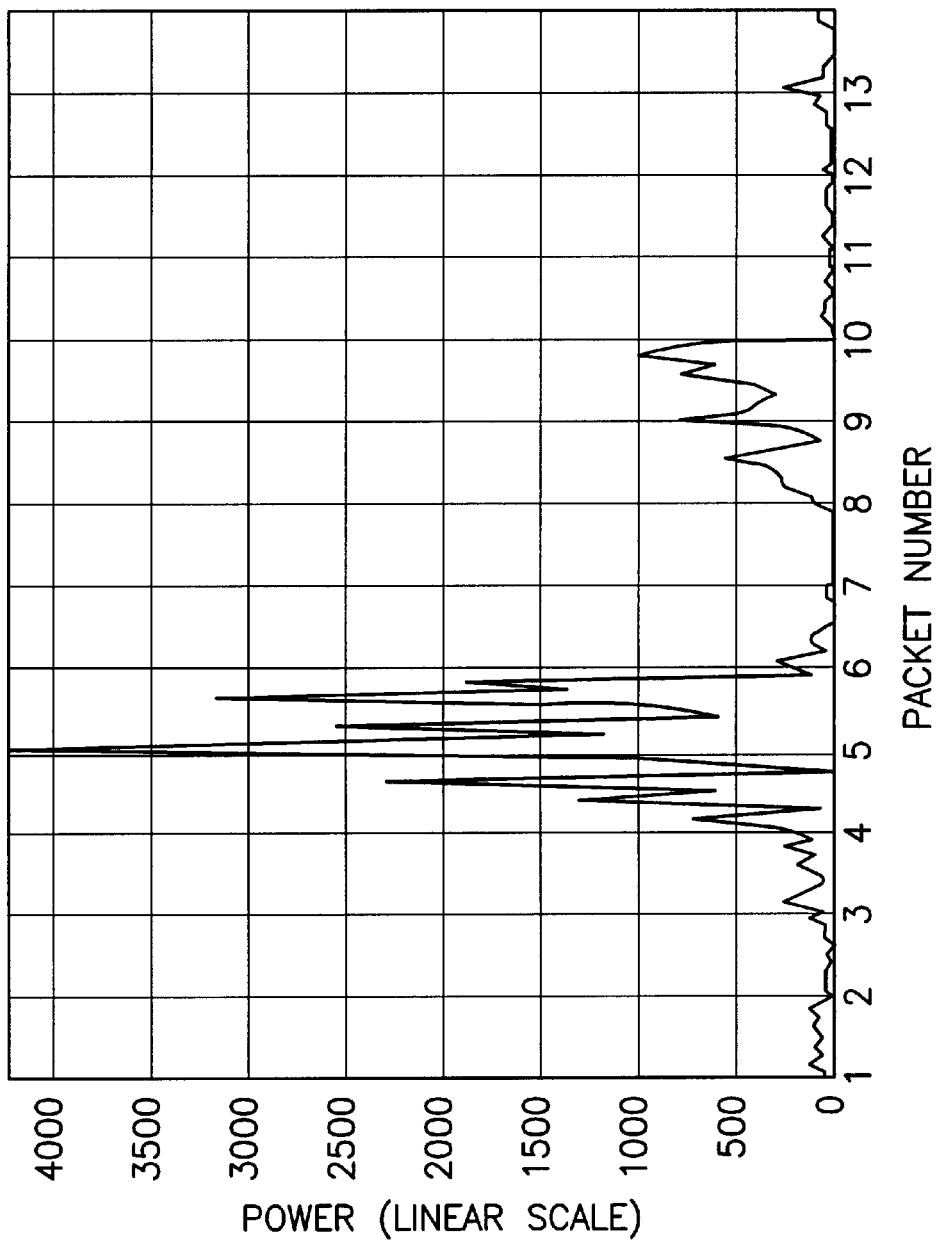
FIGS. 6–11 are graphs respectively showing the signals at points A, B, D, F, G and H in the circuitry depicted in FIG. 4.

As seen in FIG. 4, following the high-pass filter 32, the signal is amplitude detected in processor 34 where the squared magnitude of the filtered I/Q signal samples is calculated as previously described. The output of processor 34, indicated by the letter A in FIG. 4, is the speckle (power) signal shown in FIG. 6. FIG. 6 shows the power in one pixel in a linear scale. The time interval within a packet is 1/PRF. The time between each packet is 1/framerate, where framerate refers to the framerate obtained if the data is used in conventional color flow imaging. Since the power signal is the square of a zero-mean complex Gaussian process, the signal divided by the mean power (variance) is exponentially distributed with mean value equal to unity. As seen in FIG. 6, the mean power varies from packet to packet. To get a smooth temporal display, this fluctuation in the mean power needs to be compensated for. One possible way of solving this problem is indicated in FIG. 4.

In accordance with the preferred embodiment shown in FIG. 4, the power in each packet is estimated in block 46.

The power is calculated as:

$$\hat{R}(0) = \frac{1}{M}\sum_{k=0}^{M-1}|x(k)|^2$$

The difference between the squared magnitude processor 34 and the power estimation block 46 is that in the latter one mean value (i.e., one output sample) is calculated for each packet of M samples output by the high-pass filter 32. In processor 34 there is no summation. For each input sample x(k), there is a corresponding output sample which is $z(k)^2+y(k)^2$ (M input samples and M output samples).

Figure 7:
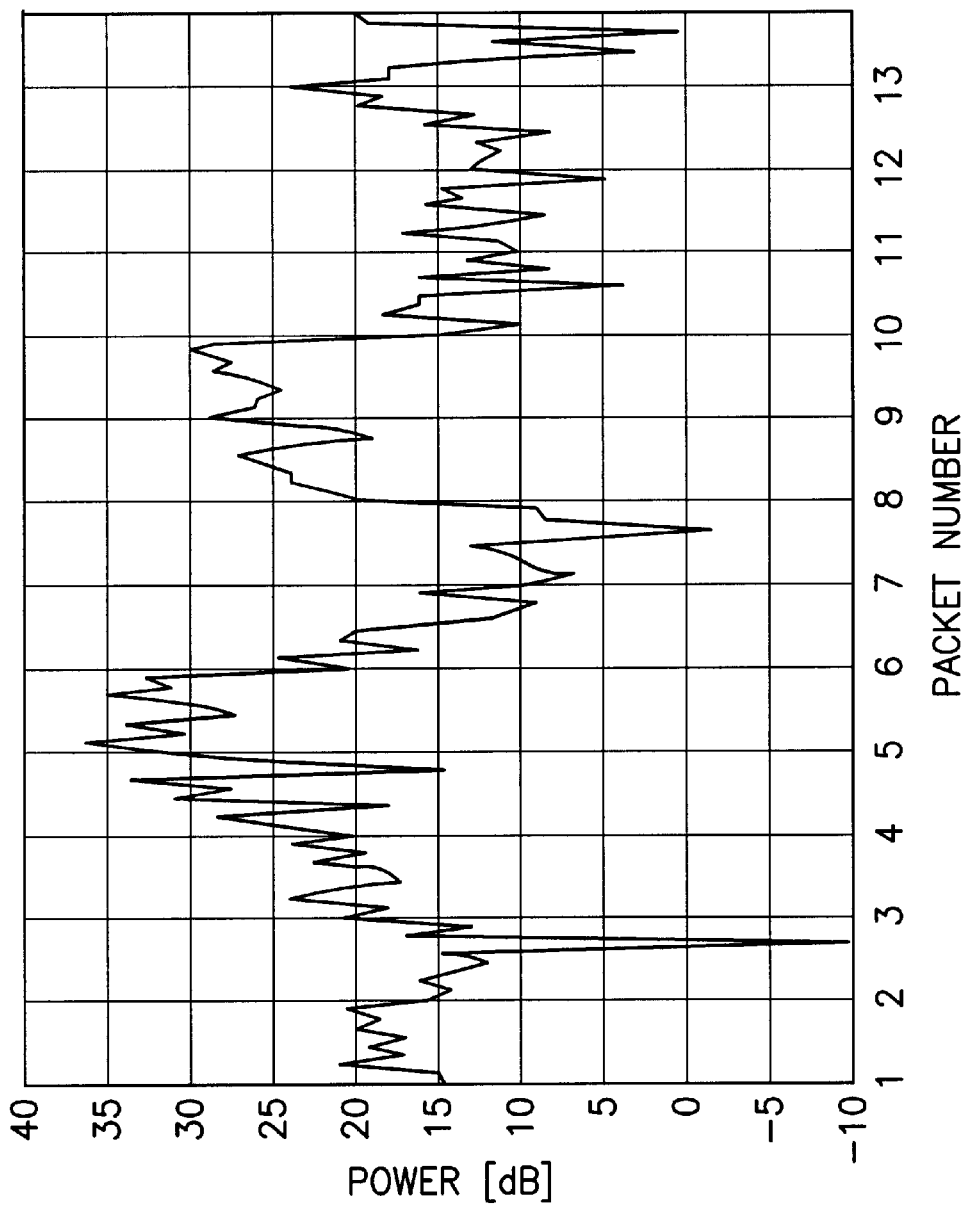
Figure 8:
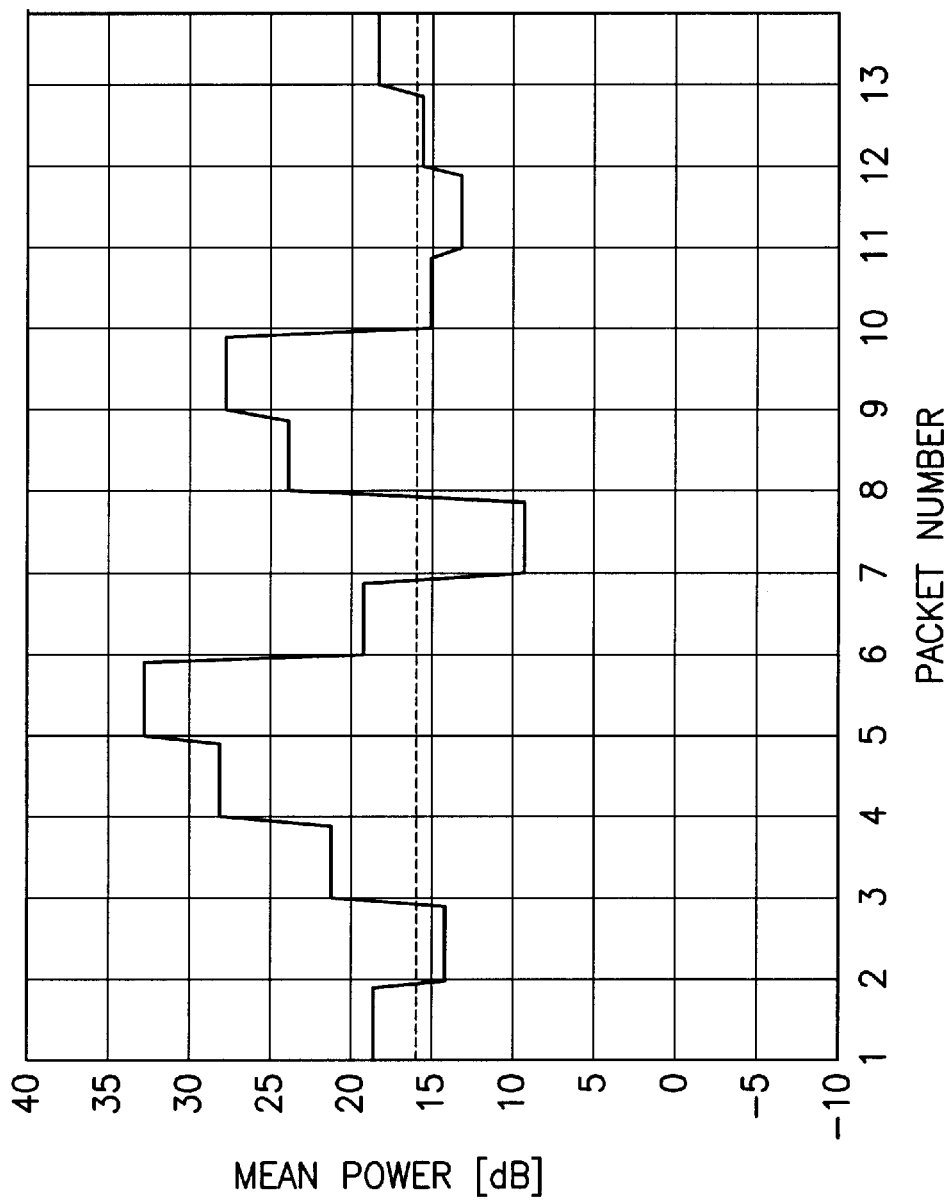
Figure 10:
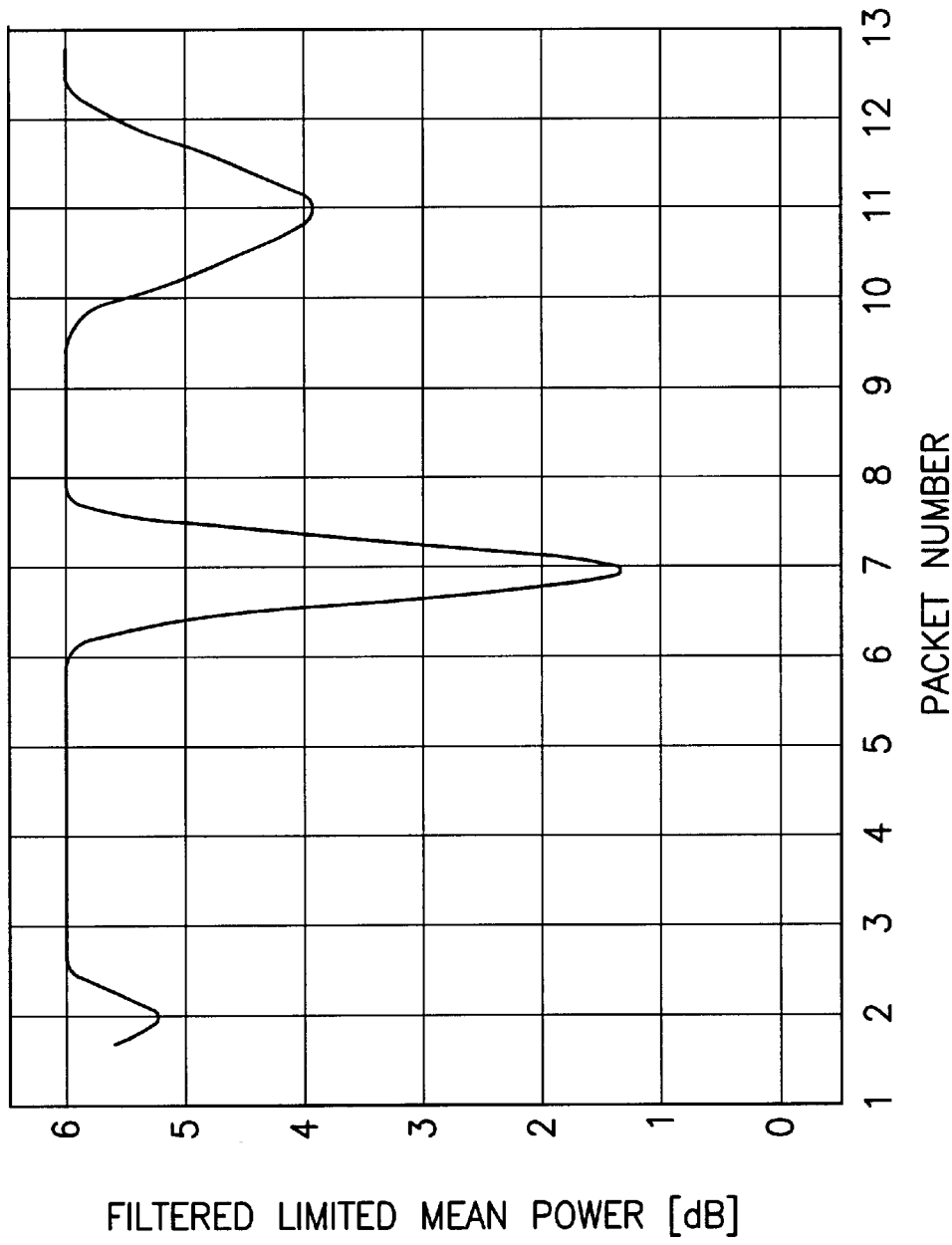

The power estimate may be spatially filtered as shown in block 48 in FIG. 4. The logarithm of both the speckle signal and the spatially filtered mean power signal are calculated in blocks 36 and 50 respectively. All of the subsequent processing is done in the log domain. Examples of the signals at points B and D in FIG. 4 are shown in FIGS. 7 and 8 respectively. (The threshold corresponding to FIG. 10 is indicated by the dashed line at 16 dB.)

Figure 9:
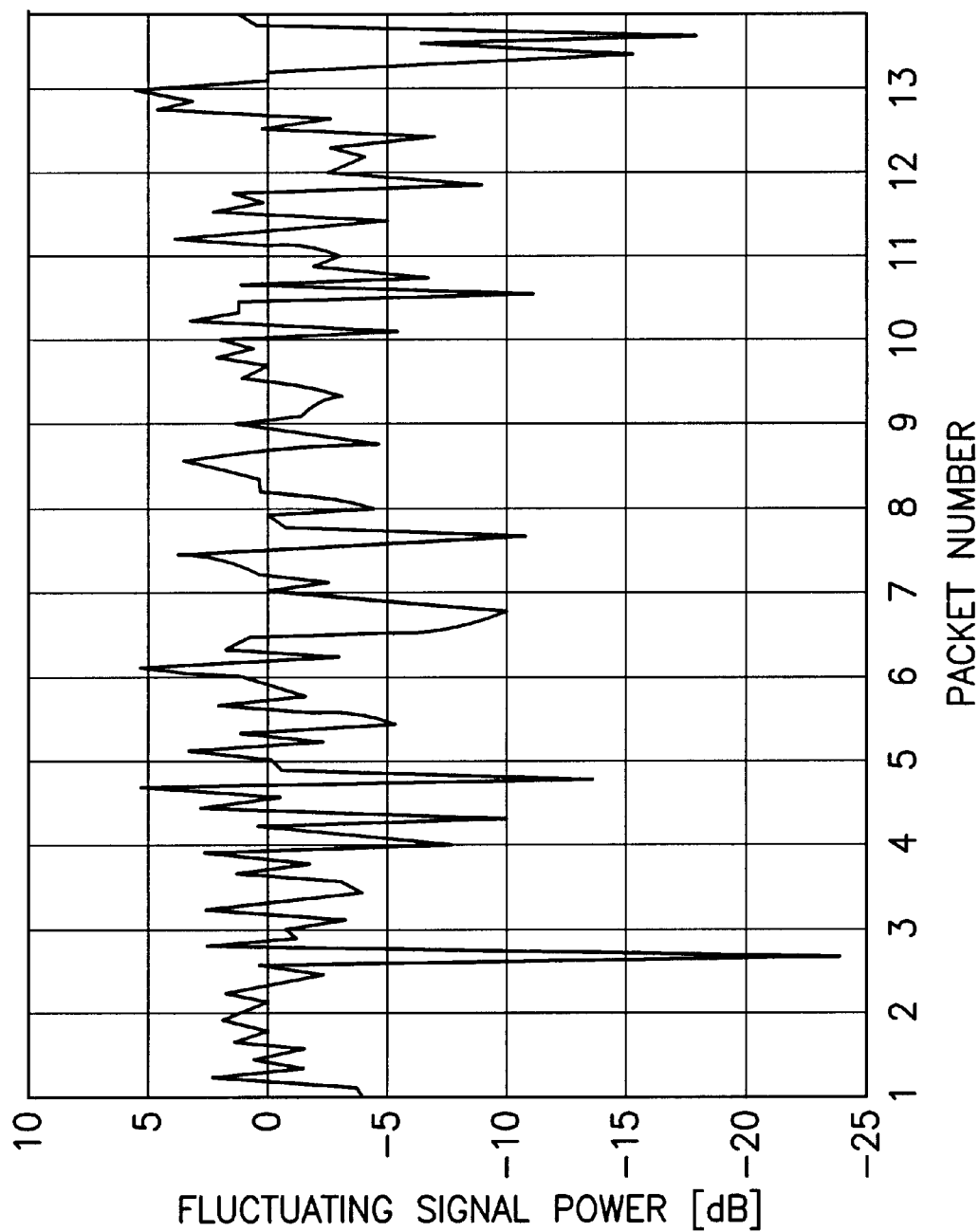

An amplitude-normalized speckle signal is obtained by subtracting the logarithm of the mean value in each packet from the logarithm of each power signal sample in the corresponding packet (see adder/subtractor 52 in FIG. 4). Subtraction in the log domain is equal to the logarithm of the fraction of the corresponding linear signals. The amplitude-normalized speckle signal (point E in FIG. 4) corresponding to the signals in FIGS. 7 and 8 is shown in FIG. 9. The samples of the speckle signal are identically distributed, where the distribution is found by a logarithmic transformation of the exponential distribution. This speckle signal may be limited to lie within a certain confidence interval determined by the probability distribution (point F in FIG. 4). The output of limiter 54 can be stored in memory without further processing, and displayed as previously described with reference to FIG. 3.

Figure 11:
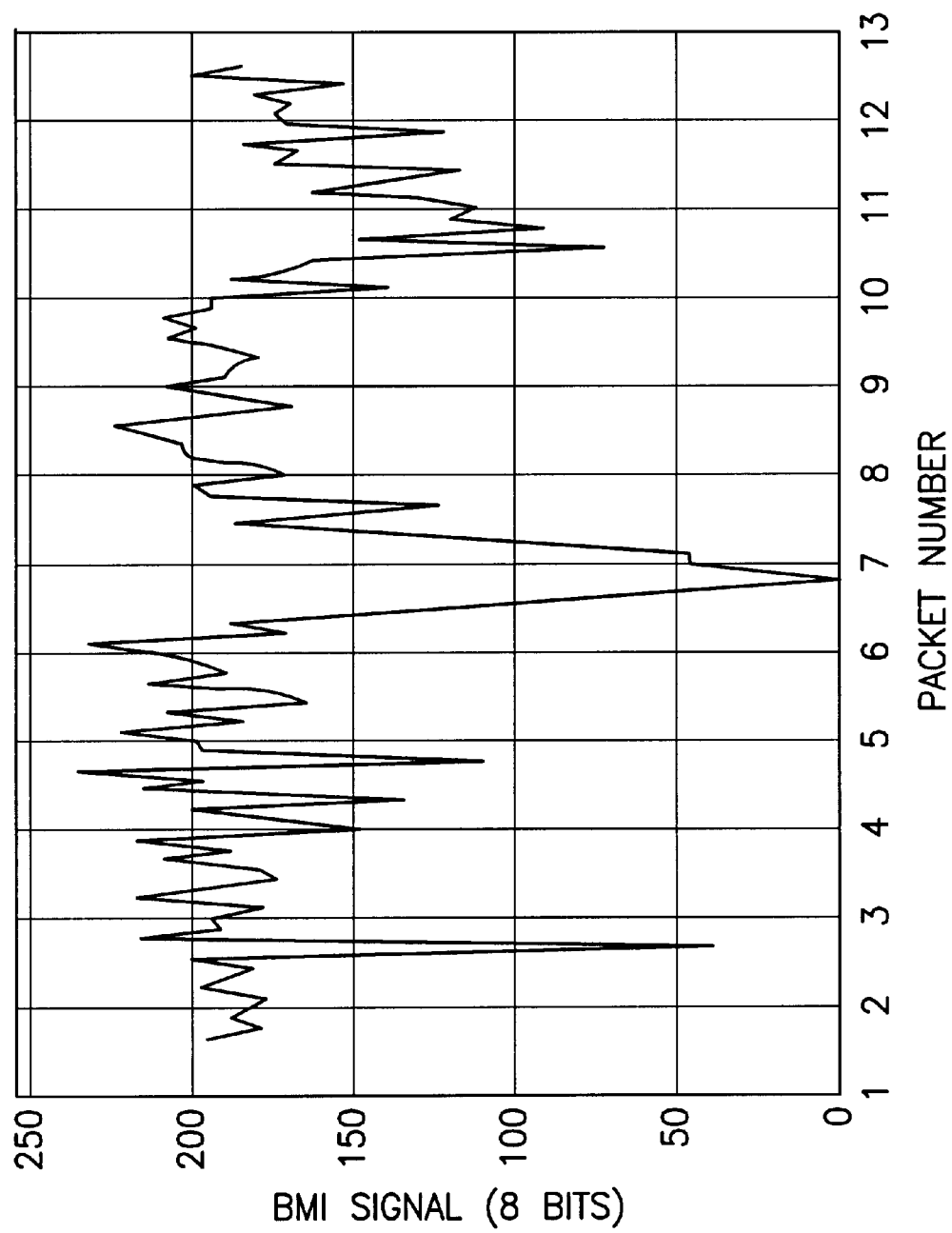

FIG. 4 depicts more advanced signal processing. The speckle signal is made visible in the flow image display by modifying the color pixel value in the areas of the image where blood flow is detected. One way of obtaining this effect is to combine the mean signal power with the speckle signal into one value which controls, for instance, the brightness of the pixel value. This can be done in the following way: Since there is only one mean power sample in each packet, it is interpolated in time (block 56) to get the same number M of mean power samples as fluctuating power samples. Gain and dynamic range may be adjusted (block 58) as in conventional color flow imaging. The signal is limited to a maximum positive value (positive limiter 60) given by the gain and dynamic range. The negative signal values are not limited to zero. The positively limited signal is then temporally smoothed by a low-pass filter 62. The interpolated, limited, and smoothed mean power signal at point G in FIG. 4 is shown in FIG. 10. The gain in this example is equal to −10 dB, and the signal is limited to a maximum value of 6 dB. The fluctuating power (i.e., speckle) signal is limited (limiter 54) and added (adder/subtractor 54) to the mean power signal, and the negative values are set equal to zero (negative limiter 66). When the mean signal has maximum value, the total signal spans the dynamic range of the display. When the mean signal is less than maximum, the smallest part of the total signal is lost. This is the enhanced speckle (i.e., BMI) signal at point H in FIG. 4. An example of the BMI signal is shown in FIG. 11.

A simpler power normalization algorithm than described in FIG. 4 is to let the BMI signal be the sum of the speckle signal output by adder/subtractor 52 and a low-pass-filtered version of the original signal at point B. In this way the interpolation is avoided.

Figure 5:
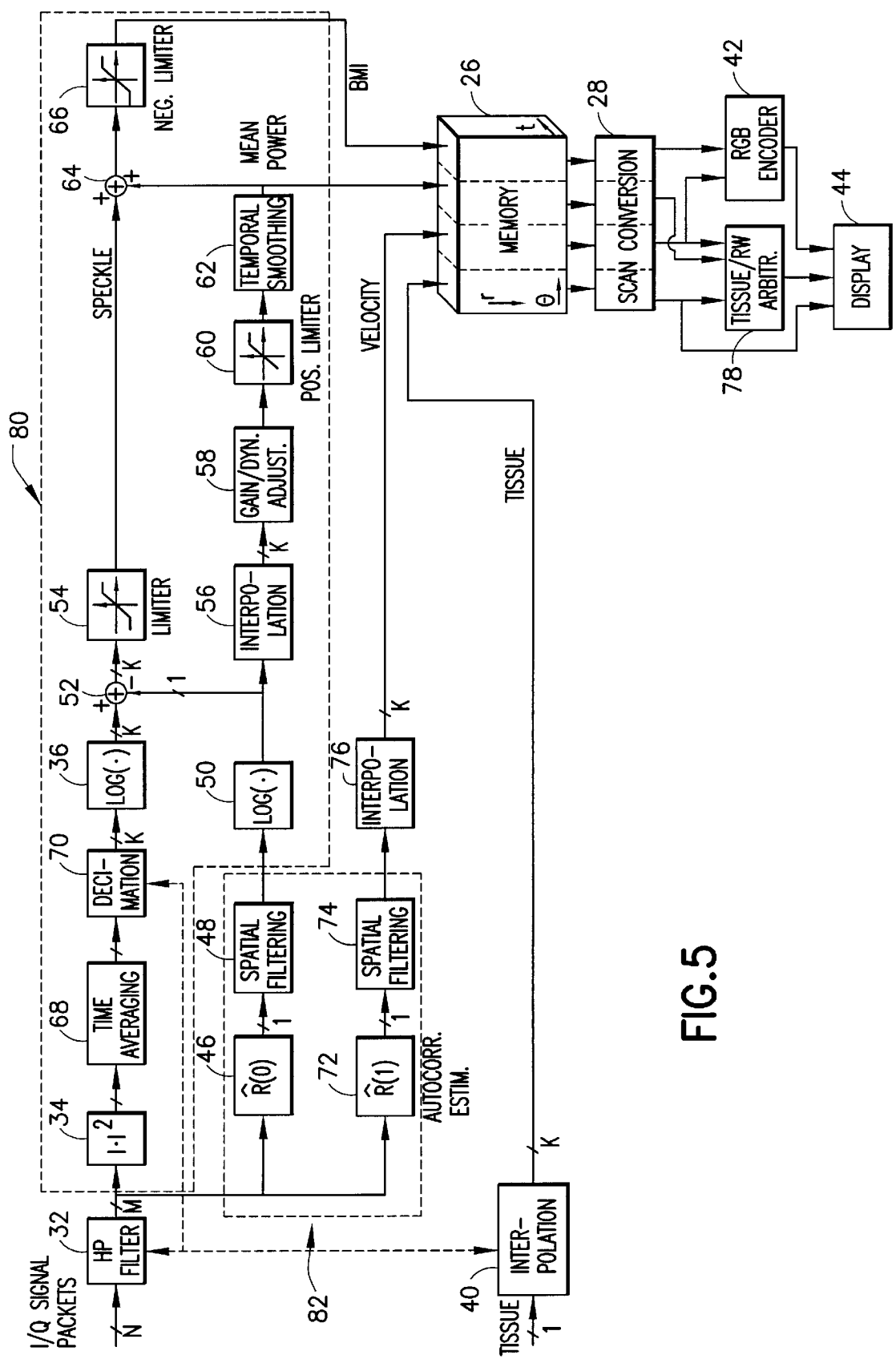
FIG. 5 is a block diagram showing yet another preferred embodiment of the invention employing advanced signal processing to produce an enhanced speckle signal which is displayed in combination with conventional color flow velocity estimates.

FIG. 5 depicts a further preferred embodiment comprising a speckle processor 80 and a conventional color flow processor 82. Blocks having the same numbers as blocks in FIG. 4 have the same function as previously described. In accordance with this preferred embodiment, temporal averaging (block 68 in FIG. 5) and decimation (block 70) may be done on the speckle signal. The temporal averaging produces lines in the speckle along the direction of the blood flow. A number of samples equal to the averaging window length is discarded after the averaging, reducing the number of samples per range gate from M to K. Further decimation may be necessary to get a frame rate suitable for real-time display. By averaging over the entire packet, the result is one sample per packet. By using the enhanced speckle signal at the output of limiter 54 as the power signal in standard color flow imaging, stripes along the flow direction are visible in the color flow images. The advantage of this alternative solution is the small difference in the processing compared to conventional color flow imaging.

In addition to the processing described above, it is possible to use the conventional autocorrelation algorithm to estimate the radial velocity component. One estimate of the autocorrelation function at temporal lag equal to one is found by autocorrelation estimator 72 from each packet as follows:

$$\hat{R}(1) = \frac{1}{M-1} \sum_{k=1}^{M-1} x(k) x * (k-1)$$

where the asterisk represents complex conjugation, e.g., if x=z+iy, then x*=z−iy. This complex-valued autocorrelation estimate is spatially filtered (block 74) and interpolated (block 76)) to produce K autocorrelation estimates. Similarly, interpolators 40 and 56 each receive one sample (i.e., the tissue and mean power signals respectively) and output K samples. The autocorrelation values are stored in memory 26, and the velocity values are calculated as a part of the display algorithm. Alternatively, the velocity values are calculated prior to memory 26, and stored instead of the autocorrelation values.

In accordance with the preferred embodiment depicted in FIG. 5, the BMI signal, mean power signal, radial velocity signal, and tissue signal are used to calculate the blood motion image for display. First, the scan conversion block 28 scan converts these four signals. Then a decision is made for each pixel whether it is a tissue pixel or a flow pixel. This tissue/flow arbitration (block 78) is based on the tissue, mean power and radial velocity signals. The RGB values of the flow pixels are determined by the BMI signal and the radial velocity signal (RGB encoder 42). The color is chosen based on the radial velocity signal, while the BMI signal determines the brightness of the color.

As previously discussed, the data are acquired using conventional packet acquisition, i.e., a series of N pulses (one packet with packet size equal to N) are transmitted in each beam direction of the flow image. The maximum possible PRF is determined by the imaging depth. By reducing the PRF, it is possible to use a technique called beam interleaving (e.g., the beam interleaving technique disclosed in U.S. Pat. No. 4,888,694). After firing a pulse in a first direction, there is time available to fire pulses in one or more different directions before firing the next pulse in the first direction. This collection of beam directions is called an interleave group. The number of beams in one interleave group is called the interleave group size. The number of interleave groups are determined by the image width and the interleave group size. Parts of the tissue image may be acquired between the different flow interleave groups, or the whole tissue image is acquired after one entire flow image acquisition. Either way, there is one tissue image recording per flow image (which consists of N pulses in each direction).

With a low PRF, the image will consist of just a few interleave groups. Combining a low PRF and small depth with a narrow image sector, an image can be acquired with just one interleave group. This is similar to flow acquisition with packet size N=1, except that it is just one tissue image per N flow pulses. Uniform sampling in time can be obtained using only one interleave group and not acquiring a separate tissue image. The tissue part of the image can then preferably be generated from the flow data using conventional tissue processing, in order to obtain a frame rate which is as high as possible. By using a relatively broad transmit beam, it is possible to form several receive beams per transmit beam by simultaneous beamforming in slightly different directions. This technique is called multi-line acquisition (MLA).

Figure 12:
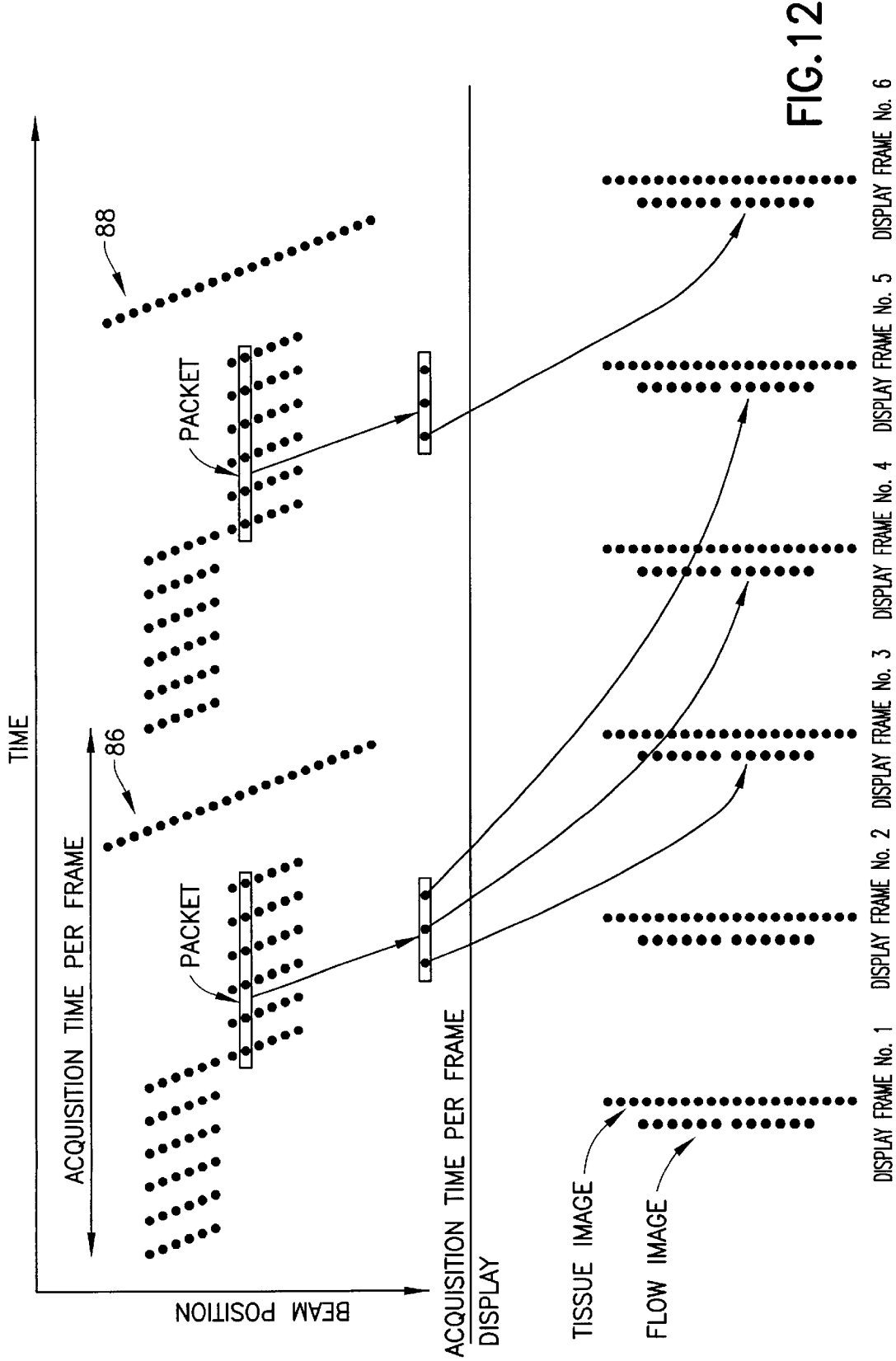
FIG. 12 is a schematic showing blood motion imaging using packet acquisition (packet size. N>1): the upper part illustrates the scanning sequence; the lower part illustrates the display sequence. The horizontal axis is the time axis and vertical axis is the beam position.

The upper part of FIG. 12 shows the scanning sequence and lower part shows the display sequence for the system depicted in FIG. 2. The horizontal axis is the time axis; the vertical axis is the beam position. In the upper part, each dot represents the received signal vector from one transmitted pulse. If MLA is used, two or more signal vectors with slightly different beam positions will be present for each time instance. FIG. 12 shows a situation without MLA (for clarity). The scanning sequence is the same as used in conventional color flow imaging. One complete scan includes a number of transmit pulses in each direction covering a certain region, and a tissue scan with one pulse in each direction, covering a larger region. In this example, the flow scan has two interleave groups each covering six beam positions. The packet size N=6. The number of signal samples after the high-pass filter M=3, which also equals the number of displayed frames per complete scan. The display frame rate will, in this example, be three times as high as in conventional color flow imaging. As shown in FIG. 12, one tissue image per blood motion imaging packet is available. This is interpolated in time to get one tissue frame per blood motion imaging frame. For example, the tissue images in display frames Nos. 3 and 6 are the same as the two tissue scans 84 and 86. The tissue images used in display frames Nos. 4 and 5 are interpolations of tissue scans 86 and 88.

Figure 13:
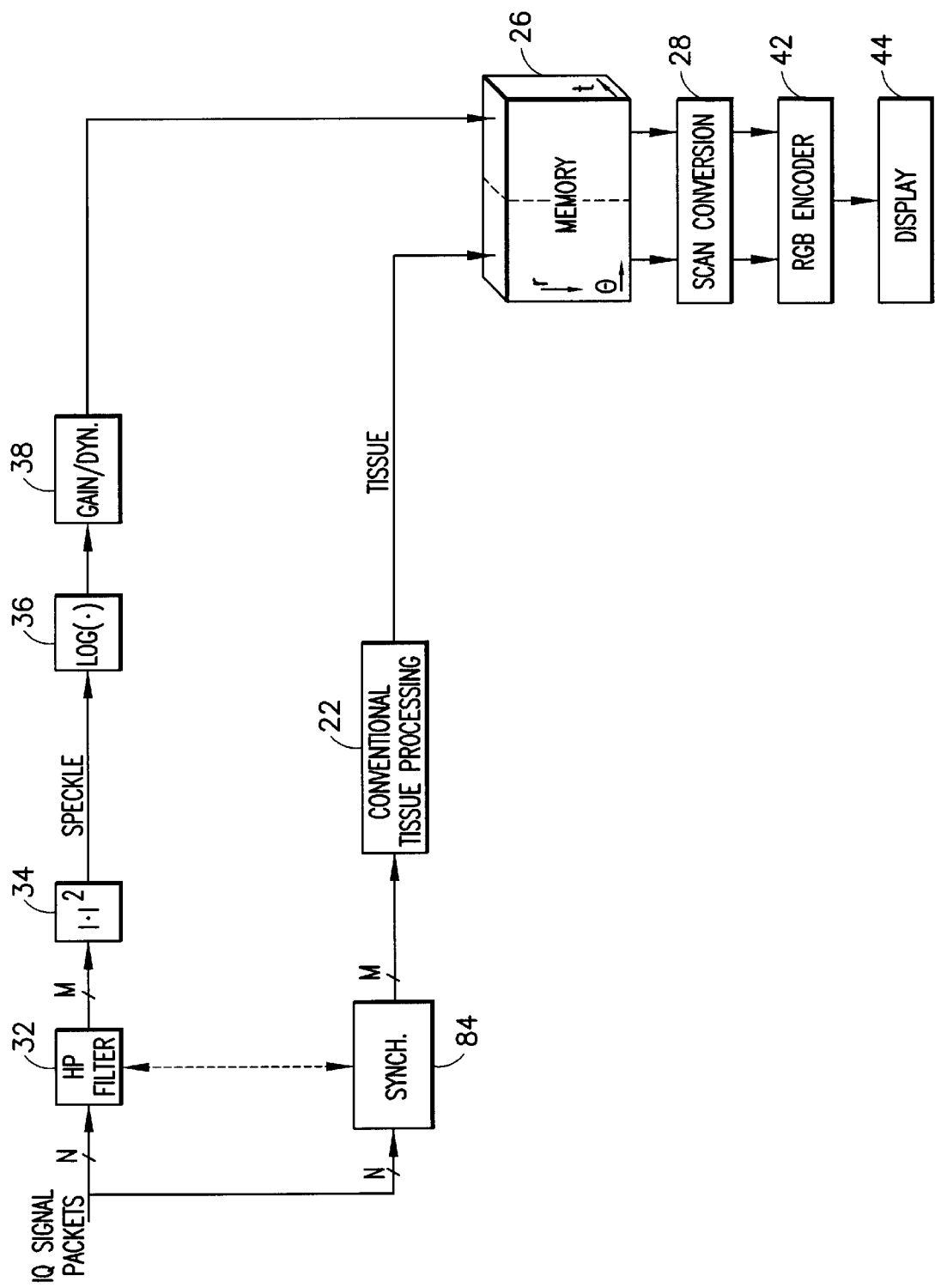
FIG. 13 is a block diagram showing one preferred embodiment of the invention for acquiring blood motion and tissue images from the same scan.

Another option is to skip the tissue scan and use the same data for both the tissue and blood motion imaging parts of the image, as indicated in FIG. 13. The synchronization block 84 first picks out the M tissue frames corresponding to the flow frames remaining after high-pass filtering. If the flow frames are decimated, the tissue frames are also decimated to K frames. In the example shown in FIG. 13, there is no decimation, i.e., the number of frames equals M. The synchronization block 84 then picks out the last M frames in the packet. Standard tissue signal processing (block 22) is then performed on the I/Q signal packets. The purpose of the synchronization block 84 is to compensate for time delay in the processing of BMI data, so that the tissue image sequence is synchronized (in time) to the blood image sequence. Tissue data could be generated like this in all the previous block diagram figures.

In accordance with the preferred embodiments disclosed herein, packet data for blood motion imaging is processed as follows. The input data are the beamformed, complex demodulated, and time-gain compensated I/Q data. Alternatively, the processing can be done on the real-valued radiofrequency (RF) data without complex demodulation. The signal from each range gate of each received beam forms a complex-valued (assuming I/Q data is used) signal vector with dimension equal to the packet size N. The signal vector thus contains samples in time from one sample volume with sampling frequency equal to the PRF. The signal samples have a zero mean complex Gaussian distribution.

The blood motion imaging method can also be used in combination with ultrasound contrast imaging. The contrast agent enhances the scattering from blood, which increases the sensitivity and make clutter filtering less critical. The blood motion imaging method may be used in combination with all known methods for contrast enhancement using a sequence of transmit pulses per scan line, including fundamental and second harmonic power Doppler, the pulse-inversion technique, and coded excitation. Variations of the echo from pulse to pulse caused by movement and/or destruction of the contrast particles will create changes in the speckle pattern in the image, which makes visual detection of small concentrations of contrast agent easier. In intermittent imaging which is often used for contrast imaging, the blood motion imaging method is of special importance, since a multiplicity of images are displayed for each recorded data set, giving a more continuous stream of images, where speckle fluctuations indicate the presence of contrast agent. Intermittent imaging means to stop the data acquisition for a defined time period between each frame. The time between each frame is typically one or several heart cycles.

The processing and display techniques described herein can be used in all combinations of imaging modalities where conventional color flow is used. Examples are M-mode and spectrum Doppler. Combination with spectrum Doppler is especially interesting, since accurate angle correction is easier to perform.

Several pulse compression techniques exist to improve the signal-to-noise ratio (SNR) without increasing the amplitude of the transmitted pulse. One such technique is described by Haider et al. in "Pulse Elongation and Deconvolution Filtering for Medical Ultrasonic Imaging," IEEE Trans. Ultrason., Ferroelect., Freq. Contr., Vol. 45, pp. 98–113, Januany 1998. The input signal to the BMI processing described herein can be acquired using such techniques which increase the SNR.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. For example, in the case where velocity estimates are to be included in the displayed information, many alternative methods of estimating the velocity are possible. The goal is to calculate K velocity estimates for each packet. This can be obtained in several ways. One possibility is to calculate one velocity estimate (by temporal averaging) per packet as in conventional color flow imaging. This is followed by interpolation to get the missing values. Another possibility is to skip the temporal averaging and get K instantaneous velocity estimates. No interpolation is then necessary. Yet another possibility is to do temporal averaging of the instantaneous velocity estimates to get a smooth signal. No interpolation is needed. Therefore, it is intended that the invention not be limited to the particular embodiment disclosed as the best mode contemplated for carrying out this invention, but that the invention will include all embodiments falling within the scope of the appended claims.

What is claimed is:

1. An imaging system comprising:

a data acquisition subsystem for acquiring sets of N data samples which are a function of ultrasound energy returned following the transmission of sets of N pulses, respective sets of N data samples being acquired for each focal position in a region of interest;

a high-pass filter coupled to said data acquisition subsystem for high-pass filtering each of said sets of N data samples to form respective sets of M filtered samples, wherein $1<M<N$;

a first processor for calculating respective sets of K signal samples from said sets of M filtered samples, wherein $1<K<M$; and a display system for displaying the K image values of a respective set in succession at a respective pixel of a multiplicity of pixels to form a succession of K images, each of said sets of K image values being derived as a function of a respective one of said sets of K signal samples.

2. The system as recited in claim 1, wherein said data acquisition system comprises a receiver and a demodulator, each of said N data samples comprising in-phase and quadrature components output by said demodulator.

3. The system as recited in claim 1, wherein said first processor comprises:

an amplitude detector for forming a respective speckle signal sample for each of said M filtered samples; and a scale converter for converting said M speckle signal samples from a linear scale to a nonlinear scale to produce M scale-converted speckle signal samples.

4. The system as recited in claim 3, further comprising:

a second processor for computing a mean power value of said M filtered samples, wherein the mean power is calculated by a method comprising temporal averaging;

a scale converter for converting said mean power value from a linear scale to a nonlinear scale; and a subtractor for subtracting said scale-converted mean power value from each of said M scale-converted speckle signal samples, thereby forming M amplitude-normalized speckle signal samples, wherein said display system displays M image values in succession at said pixel, each of said M image values being derived as a function of a corresponding one of said M amplitude-normalized speckle signal samples.

5. The system as recited in claim 4, wherein said scale converters apply a logarithmic function.

6. The system as recited in claim 4, further comprising:

a third processor for forming K power signal samples as a function of said M filtered samples from at least one packet, and for combining said K power signal samples with said K amplitude-normalized speckle signal samples to produce K enhanced speckle signal samples, wherein said display system displays K image values in succession at said pixel, each of said K image values being derived as a function of a corresponding one of said K enhanced speckle signal samples.

7. The system as recited in claim 1, wherein said data acquisition subsystem acquires a first data sample before said N data samples are acquired and a second data sample after said N data samples are acquired, said first and second data samples representing ultrasound energy returned following the transmission of respective pulses, further comprising:

a second processor for determining the magnitude of said first and second data samples to form respective first and second tissue signal samples; and an interpolator for forming (K−1) interpolated tissue signal samples based on said first and second tissue signal samples, wherein said display system displays K image values in succession at said pixel, one of said K image values being derived as a function of one of said K signal samples and one of said first and second tissue-signal samples, and another of said K image values being derived as a function of a corresponding one of the other of said K signal samples and a corresponding one of said (K−1) interpolated tissue signal samples.

8. The system as recited in claim 1, further comprising a second processor for selecting K of said N data samples prior to high-pass filtering and calculating the magnitude of each of said K selected data samples to form respective tissue signal samples, wherein said display system displays K image values in succession at said pixel, each of said K image values being derived as a function of a corresponding one of said K signal samples and a corresponding one of said K tissue signal samples.

9. The system as recited in claim 3, wherein said first processor further comprises a signal averager for forming M time-averaged speckle signal samples prior to scale conversion.

10. The system as recited in claim 3, wherein said first processor further comprises a decimator for decimating the M speckle signal samples to form K speckle signal samples, where K<M.

11. The system as recited in claim 3, further comprising a third processor for forming K velocity estimates as a function of said M filtered samples from at least one packet, wherein said display system displays K image values in succession at said pixel, each of said K image values being derived as a function of a corresponding one of said K speckle signal samples and a corresponding one of said K velocity estimates.

12. The system as recited in claim 6, further comprising:

a fourth processor for calculating K tissue signal samples; and a fifth processor for, forming K velocity estimates as a function of said M filtered samples.

13. The system as recited in claim 12, wherein said display system comprises a tissue/flow arbiter which for each of the K images determines whether a particular pixel will display a tissue signal sample or a flow signal sample based on a velocity estimate and a speckle signal sample, said arbiter making said determination based on said tissue signal sample, said power signal sample and said velocity estimate.

14. A method for imaging, comprising the steps of:

acquiring sets of N data samples which are a function of ultrasound energy returned following the transmission of sets of N pulses, respective sets of N data samples being acquired for each focal position in a region of interest;

high-pass filtering each of said sets of N data samples to form respective sets of M filtered samples, wherein $1 < M \leq N$;

calculating respective sets of K signal samples from said sets of M filtered samples, wherein $1 < K \leq M$; and displaying the K image values of a respective set in succession at a respective pixel of a multiplicity of pixels to form a succession of K images, each of said sets of K image values being derived as a function of a respective one of said sets of K signal samples.

15. The method as recited in claim 14, wherein said calculating step comprises forming a respective speckle signal sample for each of said M filtered samples, further comprising the step of converting said speckle signal samples from a linear scale to a nonlinear scale.

16. The method as recited in claim 15, further comprising the steps of:

computing a mean power value of said M filtered samples by a method comprising temporal averaging;

converting said mean power value from a linear scale to a nonlinear scale;

subtracting said scale-converted mean power value from each of said scale-converted K speckle signal samples, thereby forming K amplitude-normalized speckle signal samples; and displaying K image values in succession at said pixel, each of said K image values being derived as a function of a corresponding one of said K amplitude-normalized speckle signal samples.

17. The method as recited in claim 16, further comprising the steps of:

forming K power signal samples as a function of said M filtered samples from at least one packet;

combining said K power signal samples with said K amplitude-normalized speckle signal samples to produce K enhanced speckle signal samples; and displaying K image values in succession at said pixel, each of said K image values being derived as a function of a corresponding one of said K enhanced speckle signal samples.

18. The method as recited in claim 14, further comprising the steps of:

acquiring a first data sample before said N data samples are acquired and a second data sample after said N data samples are acquired, said first and second data samples representing ultrasound energy returned following transmission of respective pulses;

determining the magnitude of said first and second data samples to form respective first and second tissue signal samples;

forming (K−1) interpolated tissue signal samples based on said first and second tissue signal samples; and displaying K image values in succession at said pixel, one of said K image values being derived as a function of one of said K speckle signal samples and one of said first and second tissue signal samples, and another of said K image values being derived as a function of a corresponding one of the other of said K speckle signal samples and a corresponding one of said (K−1) interpolated tissue signal samples.

19. The method as recited in claim 14, further comprising the steps of:

selecting K of said N data samples prior to high-pass filtering;

calculating the magnitude of each of said K selected data samples to form respective tissue signal samples; and displaying K image values in succession at said pixel, each of said K image values being derived as a function of a corresponding one of said K speckle signal samples and a corresponding one of said K tissue signal.

20. The method as recited in claim 14, further comprising the step of forming M time-averaged speckle signal samples prior to scale converting.

21. The method as recited in claim 14, further comprising the step of decimating said M speckle signal samples to form K speckle signal samples, where K<M.

22. The method as recited in claim 14, further comprising the steps of:
forming K velocity estimates as a function of said M filtered samples from at least one packet; and
displaying K image values in succession at said pixel, each of said K image values being derived as a function of a corresponding one of said K speckle signal samples and a corresponding one of said K velocity estimates.

23. The method as recited in claim 17, further comprising the steps of:
calculating K tissue signal samples; and
forming K velocity estimates as a function of said M filtered samples.

24. The method as recited in claim 23, further comprising the step, for each of the K images, of determining whether a particular pixel will display a tissue signal sample or a flow signal sample based on a velocity estimate and a speckle signal sample, said determination being based on said tissue signal sample, said power signal sample and said velocity estimate.

25. A system for imaging blood motion comprising:
a transducer array comprising a multiplicity of transducer elements for transmitting wave energy in response to electrical activation and transducing returned wave energy into analog electrical signals;
an analog-to-digital converter for converting said analog electrical signals into digital data samples;
a display monitor for displaying an image; and
a computer programmed to perform the following steps:
controlling said transducer array to acquire sets of N data samples which are a function of ultrasound energy returned following the transmission of sets of N pulses, respective sets of N data samples being acquired for each focal position in a region of interest;
high-pass filtering each of said sets of N data samples to form respective sets of M filtered samples, wherein 1<M≦N;
calculating respective sets of K signal samples from said sets of M filtered samples, wherein 1<K<M; and
controlling said display monitor to display the K image values of a respective set in succession at a respective pixel of a multiplicity of pixels to form a succession of K images, each of said sets of K image values being derived as a function of a respective one of said sets of K signal samples.

26. The system as recited in claim 25, wherein said calculating step comprises forming a respective speckle signal sample for each of said M filtered samples, said computer being further programmed to perform the step of converting said speckle signal samples from a linear scale to a nonlinear scale.

27. The system as recited in claim 26, wherein said computer is further programmed to perform the steps of:
computing a mean power value of said M filtered samples by a method comprising temporal averaging;
converting said mean power value from a linear scale to a nonlinear scale;
subtracting said scale-converted mean power value from each of said scale-converted K speckle signal samples, thereby forming K amplitude-normalized speckle signal samples; and
controlling said display system to display K image values in succession at said pixel, each of said K image values being derived as a function of a corresponding one of said K amplitude-normalized speckle signal samples.

28. The system as recited in claim 27, wherein said computer is further programmed to perform the steps of:
forming K power signal samples as a function of said M filtered samples from at least one packet;
combining said K power signal samples with said K amplitude-normalized speckle signal samples to produce K enhanced speckle signal samples; and
controlling said display system to display K image values in succession at said pixel, each of said K image values being derived as a function of a corresponding one of said K enhanced speckle signal samples.

29. The system as recited in claim 25, wherein said computer is further programmed to perform the steps of:
controlling said transducer array to acquire a first data sample before said N data samples are acquired and a second data sample after said N data samples are acquired, said first and second data samples representing ultrasound energy returned following transmission of respective pulses;
determining the magnitude of said first and second data samples to form respective first and second tissue signal samples;
forming (K−1) interpolated tissue signal samples based on said first and second tissue signal samples; and
controlling said display system to display K image values in succession at said pixel, one of said K image values being derived as a function of one of said K speckle signal samples and one of said first and second tissue signal samples, and another of said K image values being derived as a function of a corresponding one of the other of said K speckle signal samples and a corresponding one of said (K−1) interpolated tissue signal samples.

30. The system as recited in claim 25, wherein said computer is further programmed to perform the steps of:
selecting K of said N data samples prior to high-pass filtering;
calculating the magnitude of each of said K selected data samples to form respective tissue signal samples; and
controlling said display system to display K image values in succession at said pixel, each of said K image values being derived as a function of a corresponding one of said K speckle signal samples and a corresponding one of said K tissue signals.

31. The system as recited in claim 25, wherein said computer is further programmed to perform the step of forming M time-averaged speckle signal samples prior to scale converting.

32. The system as recited in claim 25, wherein said computer is further programmed to perform the step of decimating said M speckle signal samples to form K speckle signal samples, where K<M.

33. The system as recited in claim 25, wherein said computer is further programmed to perform the steps of:
  forming K velocity estimates as a function of said M filtered samples from at least one packet; and
  controlling said display system to display K image values in succession at said pixel, each of said K image values being derived as a function of a corresponding one of said K speckle signal samples and a corresponding one of said K velocity estimates.

34. The system as recited in claim 28, wherein said computer is further programmed to perform the steps of:
  calculating K tissue signal samples; and
  forming K velocity estimates as a function of said M filtered samples.

35. The system as recited in claim 34, wherein said computer is further programmed to perform the step, for each of the K images, of determining whether a particular pixel will display a tissue signal sample or a flow signal sample based on a velocity estimate and a speckle signal sample, said determination being based on said tissue signal sample, said power signal sample and said velocity estimate.

* * * * *